United States Patent
Carlson et al.

(10) Patent No.: US 9,308,105 B2
(45) Date of Patent: Apr. 12, 2016

(54) DELIVERY DEVICE FOR AN ENDOLUMINAL PROSTHESIS

(75) Inventors: James M. Carlson, Bloomington, IN (US); Ronan T. Young, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2501 days.

(21) Appl. No.: 11/787,580

(22) Filed: Apr. 17, 2007

(65) Prior Publication Data
US 2007/0250069 A1 Oct. 25, 2007

Related U.S. Application Data

(60) Provisional application No. 60/793,197, filed on Apr. 19, 2006.

(51) Int. Cl.
*A61F 2/06* (2013.01)
*A61F 2/95* (2013.01)
*A61F 2/966* (2013.01)
*A61F 2/07* (2013.01)

(52) U.S. Cl.
CPC . *A61F 2/95* (2013.01); *A61F 2/966* (2013.01); *A61F 2/07* (2013.01); *A61F 2002/075* (2013.01); *A61F 2002/9505* (2013.01); *A61F 2002/9511* (2013.01); *A61F 2002/9517* (2013.01)

(58) Field of Classification Search
CPC ..................... A61F 2/95–2/97; A61F 2002/9505–2002/9665
USPC ................... 623/1.12, 1.11, 1.23; 606/1, 108, 606/190–200
See application file for complete search history.

(56) References Cited

U.S. PATENT DOCUMENTS

| 5,275,622 A | 1/1994 | Lazarus et al. |
| 5,534,007 A | 7/1996 | St. Germain et al. |
| 5,562,728 A * | 10/1996 | Lazarus et al. ............... 623/1.14 |
| 5,669,936 A | 9/1997 | Lazarus |
| 5,683,451 A | 11/1997 | Lenker et al. |
| 5,709,703 A * | 1/1998 | Lukic et al. .................. 623/1.12 |
| 5,749,357 A | 5/1998 | Linder |
| 5,769,882 A * | 6/1998 | Fogarty et al. ................ 128/898 |
| 6,645,238 B2 * | 11/2003 | Smith ........................... 623/1.11 |
| 6,746,478 B2 | 6/2004 | Jayaraman |

(Continued)

FOREIGN PATENT DOCUMENTS

| EP | 0 696 447 A2 | 2/1996 |
| EP | 1 637 176 A1 | 3/2006 |

(Continued)

OTHER PUBLICATIONS

Browne, T. F. et al.; "A Fenestrated Covered Suprarenal Aortic Stent;" Eur. J. Vasc. Endovasc. Surg. 18; pp. 445-449 (1999).

*Primary Examiner* — Katherine Rodjom
*Assistant Examiner* — Jonathan Hollm
(74) *Attorney, Agent, or Firm* — Brinks Gilson & Lione

(57) ABSTRACT

A system for endoluminally delivering and deploying a prosthesis includes a prosthesis comprising a self-expanding stent and a cover for retaining at least a portion of the self-expanding stent. The stent is biased into contact with an inner surface of the cover. The inner surface has a hardness that is equal to or greater than the hardness of the stent. Additional aspects of the invention are disclosed and include a method of manufacturing an endoluminal prosthesis delivery and deployment system.

10 Claims, 14 Drawing Sheets

(56) References Cited

U.S. PATENT DOCUMENTS

| | | |
|---|---|---|
| 2002/0077643 A1* | 6/2002 | Rabiner et al. .............. 606/169 |
| 2002/0082684 A1* | 6/2002 | Mishaly ...................... 623/1.36 |
| 2002/0183827 A1 | 12/2002 | Derus et al. |
| 2003/0233140 A1 | 12/2003 | Hartley et al. |
| 2004/0098079 A1 | 5/2004 | Hartley et al. |
| 2004/0106974 A1 | 6/2004 | Greenberg et al. |
| 2005/0060018 A1 | 3/2005 | Dittman |
| 2005/0085890 A1 | 4/2005 | Rasmussen et al. |
| 2005/0107862 A1 | 5/2005 | Ohlenschlaeger |
| 2006/0265042 A1* | 11/2006 | Catanese et al. ............ 623/1.11 |

FOREIGN PATENT DOCUMENTS

| | | |
|---|---|---|
| EP | 1 810 644 A2 | 7/2007 |
| WO | WO 98/53761 A1 | 12/1998 |
| WO | WO 03/005936 A2 | 1/2003 |
| WO | WO 03005936 A2 * | 1/2003 |
| WO | WO 2006107608 A1 * | 10/2006 |

\* cited by examiner

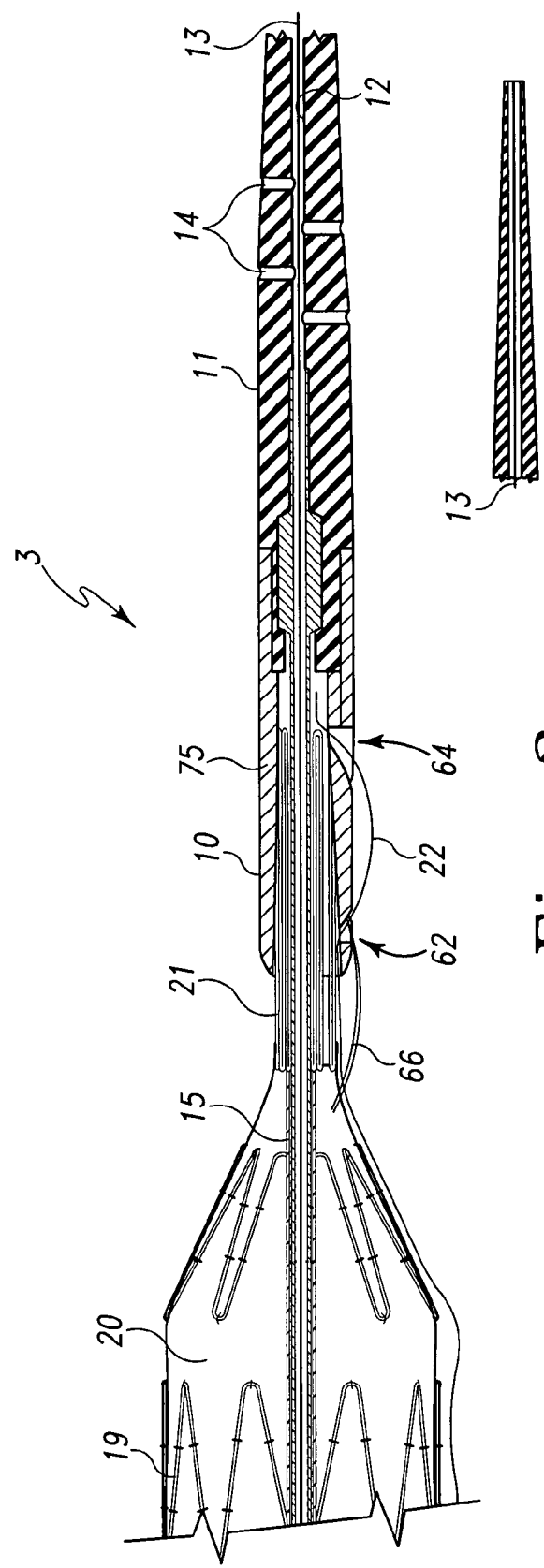

DELIVERY DEVICE FOR AN ENDOLUMINAL PROSTHESIS

RELATED APPLICATIONS

This application claims the benefit of the filing date under 35 U.S.C. §119(e) of U.S. Provisional Patent Application Ser. No. 60/793,197, filed Apr. 19, 2006, which is incorporated herein by reference.

BACKGROUND OF THE INVENTION

1. Field of the Invention

This invention relates to a medical device, and in particular to a delivery device for an endoluminal prosthesis.

2. Description of Related Art

The deployment of endoluminal prostheses into the lumen of a patient from a remote location by the use of a deployment device is generally known. An endoluminal prosthesis may be retained in a radially constrained state within a sleeve until it is deployed. To deploy the prosthesis, the sleeve is withdrawn from the prosthesis allowing the prosthesis to expand. The prosthesis may be radially self-expanding or it may be balloon expandable. The prosthesis may comprise a graft and/or a stent.

U.S. Published Patent Application Nos. 20040098079, 20040106974, 20050085890, and 20050060018, which are herein incorporated by reference, disclose various delivery devices for an expandable endoluminal prosthesis. The expandable endovascular prosthesis comprises a bare self-expanding stent disposed on an end portion thereof. The self-expanding stent may comprise a plurality of barbs that in use are adapted to anchor the prosthesis to a surrounding body lumen. A cover retains an end portion of the self-expanding stent on the delivery device in a radially constrained state. To deploy the prosthesis, the operator withdraws the cover from the self-expanding stent, thereby exposing the stent and allowing it to expand radially outwardly.

The stent radially expands against an inner surface of the cover prior to deployment. The expansion force of the stent against the inner surface can be sufficiently high so as to create significant interference between the stent and the cover. This can result in increased operating effort to remove the cover from the stent. This is particularly true where the stent comprises sharpened barbs that may scratch or dig into the inner surface of the cover.

SUMMARY

According to an aspect of the present invention, a system for endoluminally delivering and deploying a prosthesis is provided and comprises a prosthesis and a cover. The prosthesis comprises a body portion and an end portion including a self-expanding stent. The cover maintains at least a portion of the stent in a compressed state until deployment and has a generally tubular cavity that defines an inner surface. The stent is biased into contact with the inner surface which has a hardness that is equal to or greater than the hardness of the stent. Accordingly, the stent cannot dig into the cover and the operating effort to remove the cover from the prosthesis will be reduced.

The stent may be made from any suitable material, such as stainless steel or nitinol. According to an aspect of the invention, the inner surface of the cover comprises a metal, a metal alloy, or a ceramic. In a preferred embodiment, the inner surface comprises anodized aluminum and may optionally comprise PTFE. According to an aspect of the invention, the cover may comprise a plastic body with a metal inner surface.

The stent may comprise a plurality of radially-disposed barbs for anchoring the stent within the lumen. The barbs engage the inner surface of the cover until deployment. Because the inner surface is generally as hard, or harder than the stent, a particularly aggressive stent or barb design may be used in conjunction with the cover. According to another aspect of the invention, at least a portion of the prosthesis may be radially disposed within the lumen of a sheath in a compressed configuration.

According to another aspect of the present invention, a method of manufacturing an endoluminal prosthesis delivery and deployment system is provided. The method comprises the steps of providing a prosthesis having a proximal end and a distal end, and providing a cover. At least one of the proximal and distal ends of the prosthesis includes a self-expanding stent. The cover has a cavity that defines an inner surface having a hardness that is equal to or greater than the hardness of the stent. The method further comprises the step of retaining at least a portion of the stent within the cavity of the cover so that the stent is biased into contact with the inner surface.

The stent and the cover may comprise any suitable material, as described above. For example, the stent may comprise stainless steel and the inner surface of the cover may be made of anodized aluminum and PTFE.

According to one aspect of the invention, the cover providing step may include inserting a metal bushing into the cavity so that an inner lumen of the bushing defines the inner surface of the cover. According to another aspect of the invention, the cover providing step may include applying a metallized coating to the cavity to form the inner surface.

BRIEF DESCRIPTION OF THE DRAWINGS

FIG. 3 is a sectional detail view of a portion of the delivery device of FIG. 1 around the distal end of the prosthesis;

DETAILED DESCRIPTION OF PREFERRED EMBODIMENTS

Throughout the specification, the terms "distal" and "distally" shall denote a position, direction, or orientation that is generally toward the patient. Accordingly, the terms "proximal" and "proximally" shall denote a position, direction, or orientation that is generally away from the patient.

Figure 1:
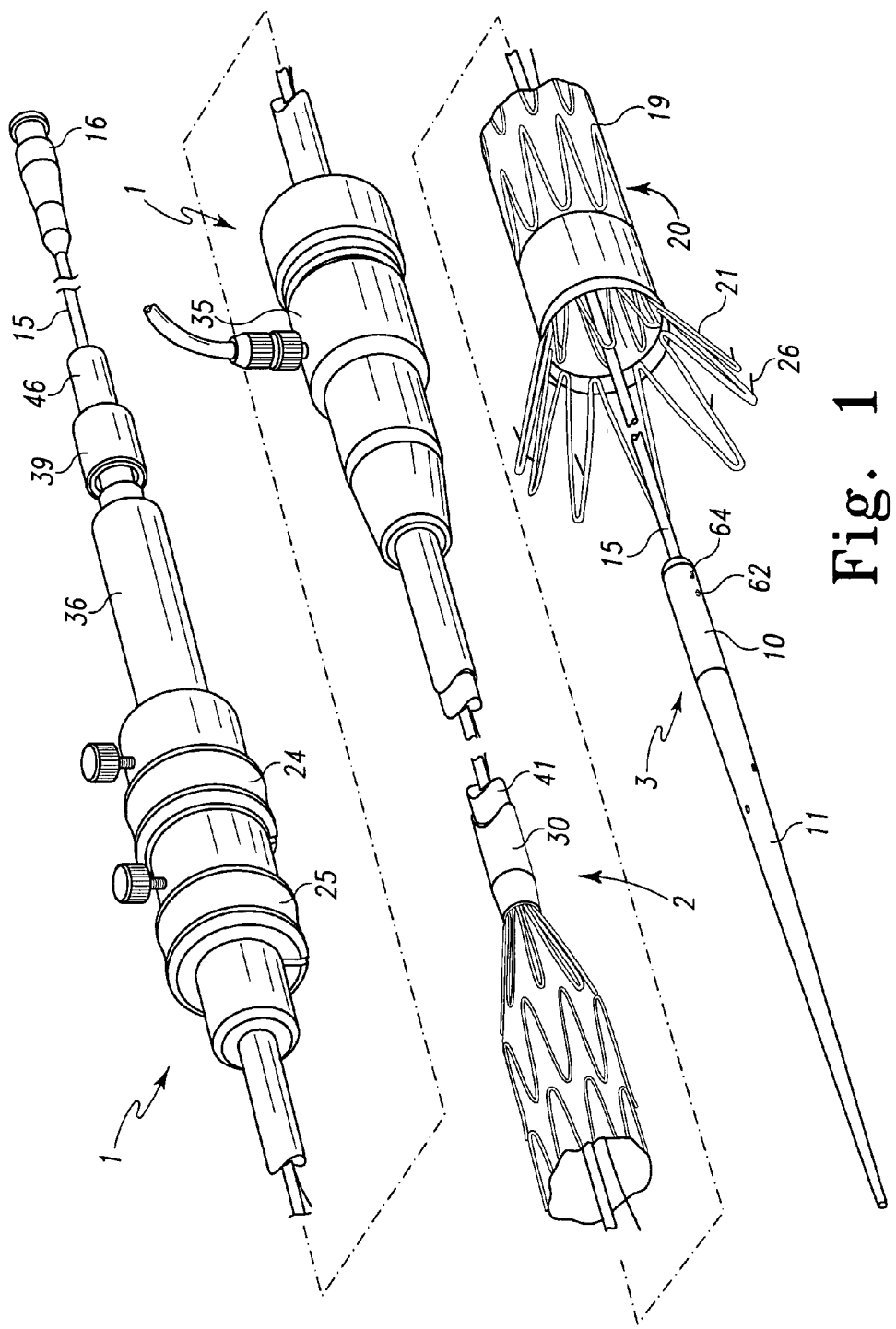
FIG. 1 is a perspective view of a delivery device according to an aspect of the present invention.

FIG. 1 shows an endovascular delivery device which can be used for delivering and deploying a prosthesis 20 in a lumen of a patient. The delivery device includes an external manipulation section 1, a proximal positioning mechanism or attachment region 2, and a distal positioning mechanism or attachment region 3. During a medical procedure to deploy the prosthesis 20, the proximal and distal attachment regions 2 and 3 will travel through the lumen to a desired deployment site. The external manipulation section 1, which is acted upon by a user to manipulate the delivery device, remains outside of the patient throughout the procedure.

The prosthesis 20 can comprise a tubular graft material, such as Dacron, with self-expanding stents 19 attached thereto. The self-expanding stents 19 cause the prosthesis 20 to expand when released from the delivery device. The self-expanding stents 19 may be disposed on the interior surface of the tubular graft material. Alternately, the stents 19 may be disposed on the exterior surface of the tubular graft material. The prosthesis 20 also includes an exposed self-expanding zigzag stent 21, which is a bare wire stent. The self-expanding stent 21 may have barbs 26 that extend from the stent distal end. When the self-expanding stent 21 is released, the barbs 26 anchor the distal end of the prosthesis 20 to the surrounding lumen (not shown). Self-expanding stents 19, 21 are generally made of metal. For example, self-expanding stents 19, 21 may comprise stainless steel, nitinol, or the like.

A sheath 30 retains the prosthesis 20 in a compressed condition on the delivery device. The sheath 30 comprises a generally elongate tubular body. The prosthesis 20 is disposed within the sheath lumen. The prosthesis 20 and the self-expanding stents 19 radially expand against the inner surface of the sheath 30. The sheath 30 preferably comprises a flexible material so that in use it is able to negotiate tortuous inner body lumina. The sheath 30 may also comprise a lubricious or slippery material to facilitate insertion and withdrawal of the thick walled tube 41 and of catheters and the like therethrough. Accordingly, the sheath 30 may comprise a plastic material, such as polytetrafluoroethylene (PTFE), polyethylene, nylon, or the like.

The sheath 30 radially compresses the prosthesis 20 over a distal portion of a thin walled tube 15. The thin walled tube 15 is generally flexible and may be made of metal, for example stainless steel or nitinol. A tube 41, which can be made of plastic, is coaxial with and radially outside the thin walled tube 15. The distal end of the tube 41 is adjacent the proximal end of the prosthesis 20.

Figure 5:
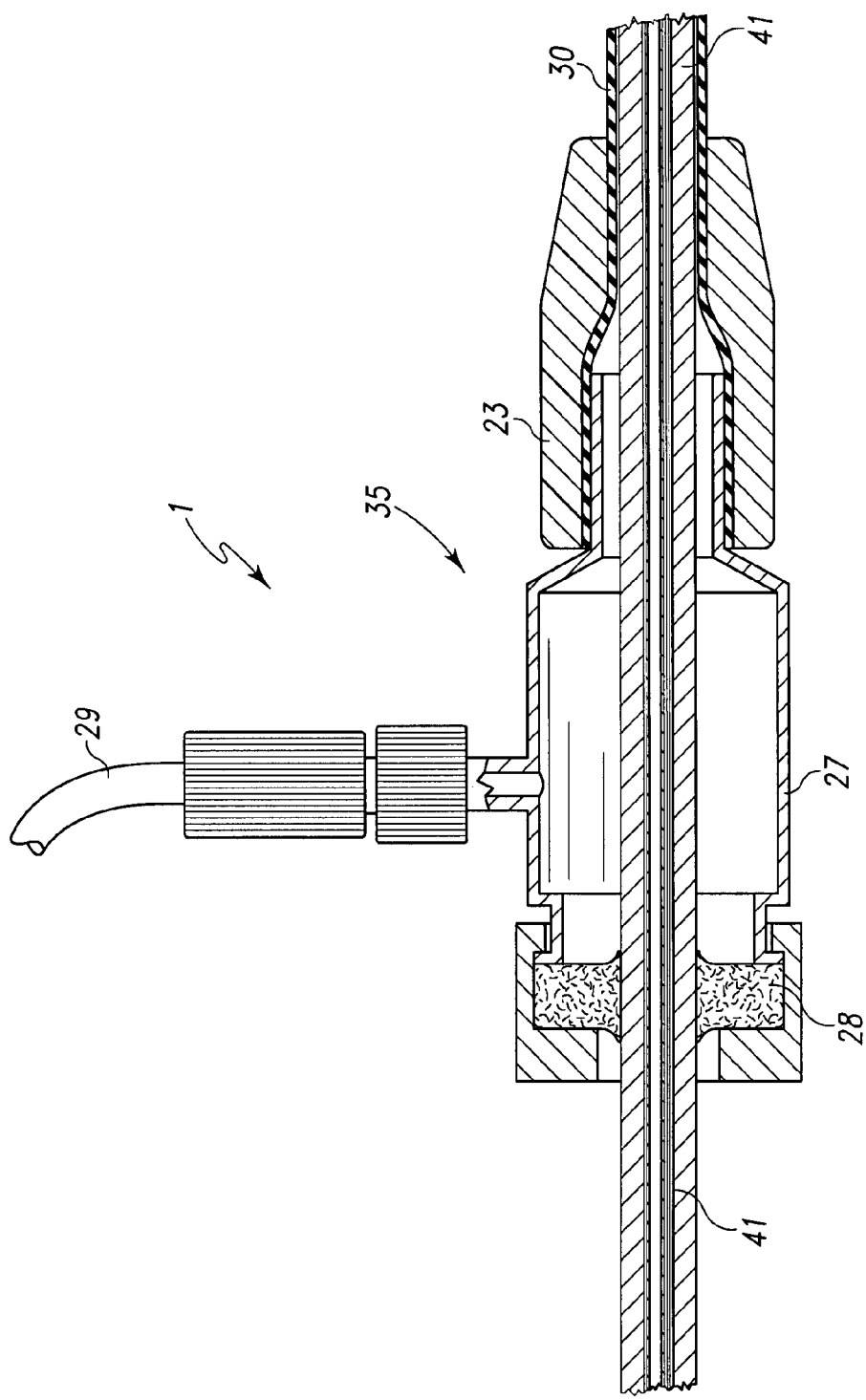
FIG. 5 is a sectional view of a portion of the delivery device of FIG. 1 around the haemostatic seal.
Figure 7:
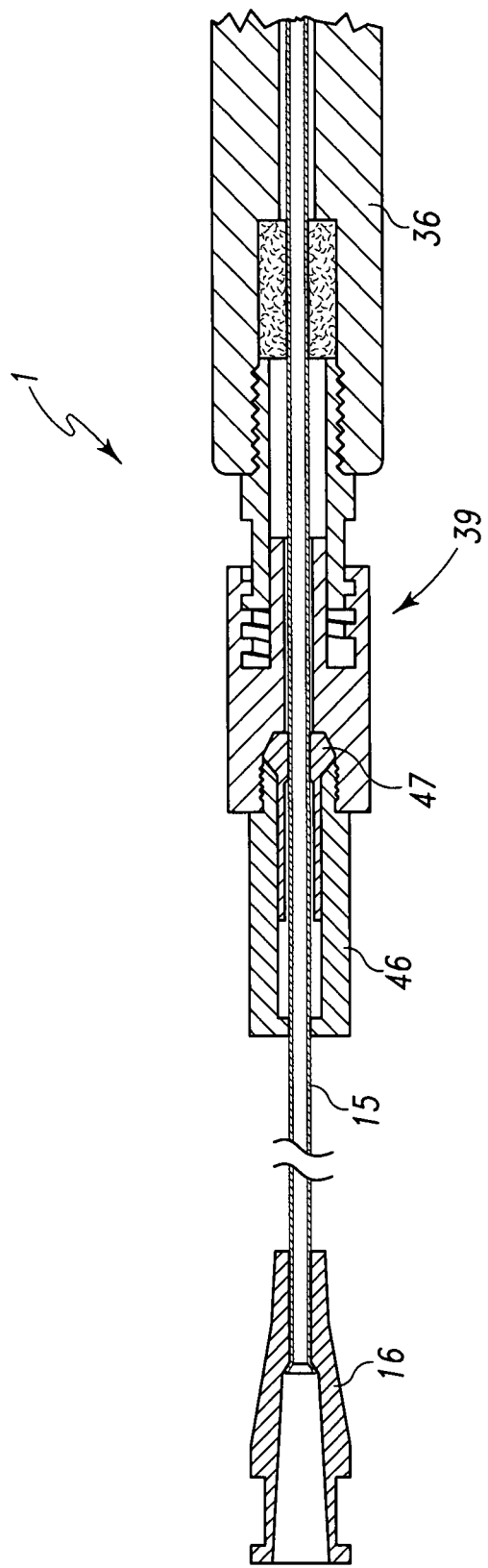
FIG. 7 is a sectional view of a portion of the delivery device of FIG. 1 around the pin vise clamp and the medical reagent introduction tube.

The tube 41 is "thick walled", which is to say the thickness of the wall of tube 41 is several times that of the thin walled tube 15. Preferably, the tube 41 is five or more times thicker than the thin walled tube 15. The sheath 30 is coaxial with and radially outside the thick walled tube 41. The thick walled tube 41 and the sheath 30 extend proximally to the manipulation region 1, as shown in FIG. 5. The thin walled tube 15 extends proximally to the proximal end of the delivery device, as shown in FIG. 7. The delivery device further includes haemostatic sealing means 35 radially disposed about the sheath and the thick walled tube 41, as shown in FIG. 5. The haemostatic sealing means 35 controls the loss of blood through the delivery device during a procedure.

Figure 2:
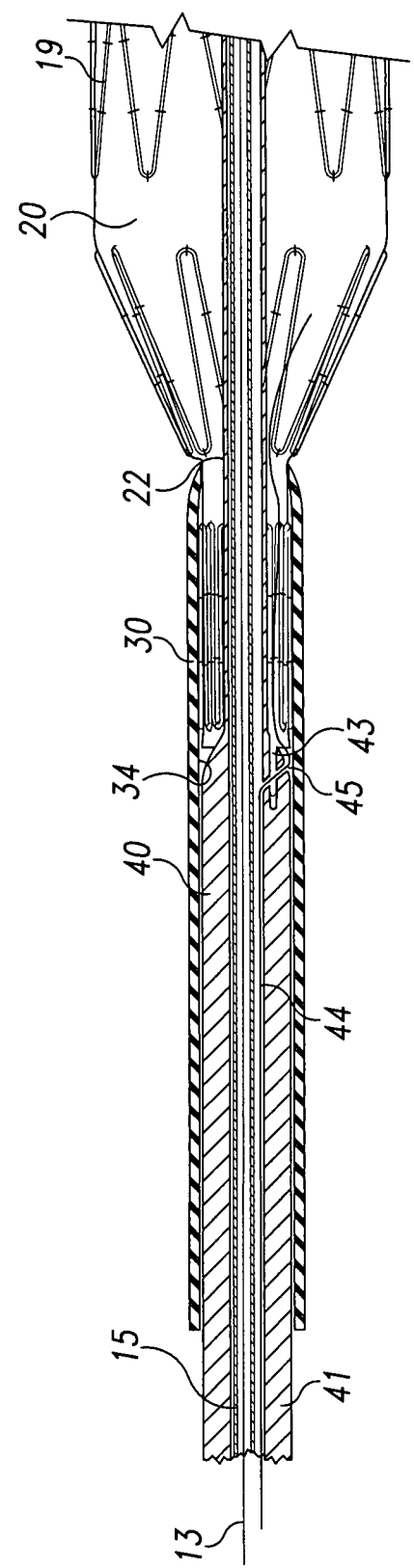
FIG. 2 is a sectional detail view of a portion of the delivery device of FIG. 1 around the proximal end of the prosthesis.

FIG. 2 illustrates a proximal prosthesis retention and release mechanism. The proximal retention section 40 radially and axially retains a proximal end of the prosthesis 20 during the procedure. The proximal retention section 40 may comprise the thick walled tube 41, as shown in FIG. 2. Alternately, the proximal retention section 40 may comprise a separate body coupled to the thick walled tube 41. The proximal end of the prosthesis 20 comprises an aperture defining a loop 43. A proximal trigger wire 44 extends through the loop 43 and through an aperture 45 in the proximal attachment section 40 into an annular region between the thin walled tube 15 and the thick walled tube 41. The proximal trigger wire 44 extends proximally through the delivery device from the proximal retention section 40 to the release wire actuation section located in the external manipulation section 1 (see FIG. 1). The trigger wire 44 couples the proximal end of the prosthesis 20 to the proximal retention section 40 during deployment to limit axial and radial displacement of the prosthesis. The prosthesis 20 can be selectively released into the body lumen by disengaging the trigger wire 44 from the loop 43.

FIG. 3 illustrates a distal retention and release mechanism. The distal attachment region 3 includes a retention device 10. The retention device 10 radially and axially retains the distal end of the self-expanding zigzag stent 21 during a procedure. The retention device 10 comprises a cover 75. A distal portion of the self-expanding zigzag stent 21 is compressed within the cover 75. The retention device 10 may comprise suture loops 66 and a distal trigger wire 22 for coupling the stent 21 to the cover 75 to prevent inadvertent early deployment.

The retention device 10 has at its distal end a long tapered flexible extension 11, as shown in FIG. 3. The flexible extension 11 comprises an internal longitudinal aperture 12. The longitudinal aperture 12 facilitates advancement of the tapered flexible extension 11 along a previously inserted insertion wire 13. The longitudinal aperture 12 also provides a channel for the introduction of medical reagents. For example, it may be desirable to supply a contrast agent to allow angiography to be performed during placement and deployment phases of the medical procedure.

The distal end of the thin walled tube 15 is coupled to the flexible extension 11. The thin walled tube 15 is flexible so that the delivery device can be advanced within a relatively tortuous vessel, such as a femoral artery. The thin walled tube extends proximally through the delivery device to the manipulation section 1, terminating at a connection means 16, as shown in FIG. 7. The thin walled tube 15 is in mechanical communication with the flexible extension, allowing the operator to axially and rotationally manipulate the distal attachment region 3 with respect to the prosthesis 20. The connection means 16 is adapted to accept a syringe to facilitate the introduction of reagents into the thin walled tube 15. The thin walled tube 15 is in fluid communication with the aperture 12 of the flexible extension 11. Therefore, reagents introduced into connection means 16 may pass through aperture 12 and can emanate from lateral apertures 14 into the body lumen.

Figure 4A:
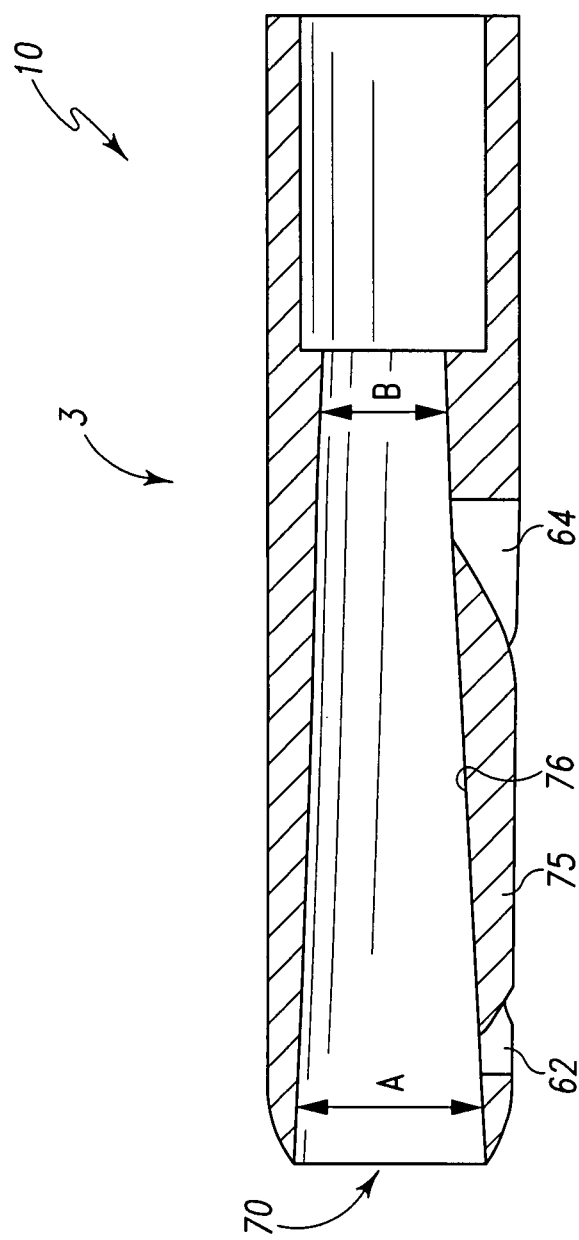
FIG. 4A is a sectional view of a distal retention device of the delivery device of FIG. 1.
Figure 4B:
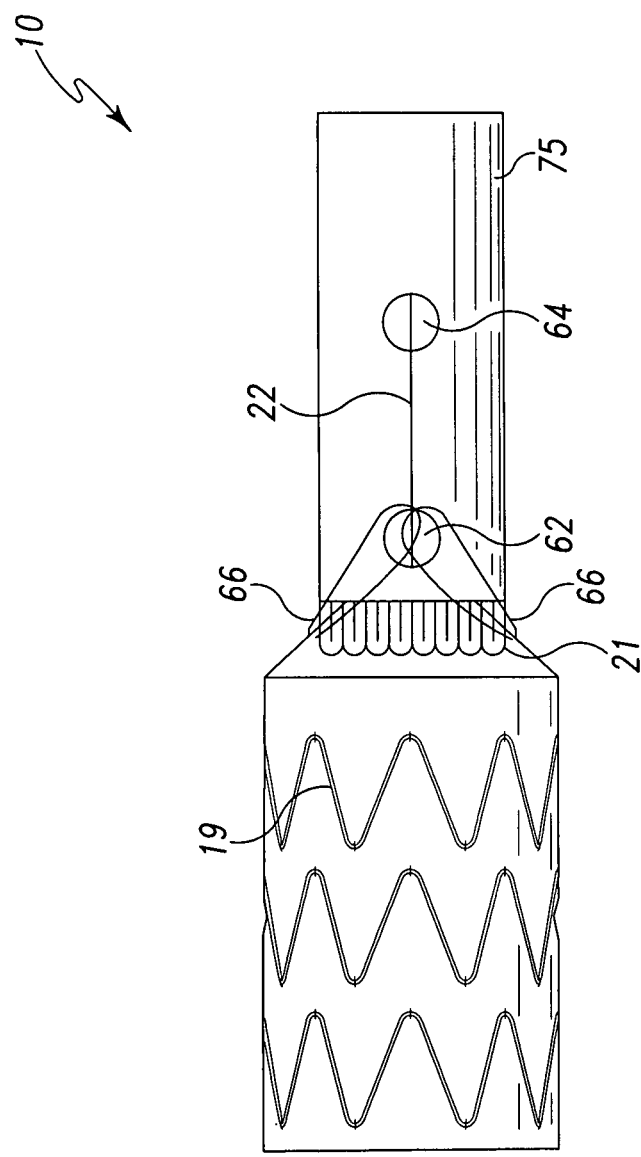
FIG. 4B is a plan view of the distal retention device of the delivery device of FIG. 1.

FIG. 4B is a plan view of the retention device 10 showing the prosthesis 20 partially deployed, with the self-expanding zigzag stent 21 still retained in a compressed state. The distal retention device 10 includes apertures 62 and 64 to accommodate the distal trigger wire 22. The suture loops 66 are coupled to the body of the prosthesis 20, and hold the self-expanding zigzag stent 21 in the retention device 10 until the trigger wire 22 is removed. While the trigger wire 22 is in place, the suture loops 66 prevent the retention device 10 and the prosthesis 20 from separating. The trigger wire 22 retains the suture loops 66 against an outer surface of the retention device 10. The distal trigger wire 22 extends proximally through the delivery device from the distal retention device 10 to a release wire actuation section located in the manipulation section 1 (see FIG. 1).

As shown in FIG. 4B, the suture loops 66 are attached to opposing sides of the prosthesis 20, for example separated by 90 to 180 degrees. The suture loops 66 are generally inelastic and do not stretch. Since the suture loops 66 do not stretch, they provide opposing torques, thereby preventing the prosthesis 20 from rotating within the retention device 10. This configuration differs from delivery devices that have a single point of attachment. Such devices may allow the stent to rotate within the retention device and lead to entanglement of the stent's struts. When the trigger wire 22 is removed, the suture loops 66 are free to move. The retention device 10 may then be released from the self-expanding zigzag stent 21 by sliding the retention device 10 distally away from the prosthesis 20.

The cover 75 includes an opening that extends longitudinally to form the surface of a cavity 70, as shown in FIG. 4A. The cavity 70 defines an inner surface 76. The cavity 70 may have a generally tubular shape, or it may comprise a generally conical or frustoconical shape, as shown in FIG. 4A. The cavity 70 shown in FIG. 4A decreases linearly in diameter from a maximum diameter A near the proximal opening to a minimum diameter B near the distal end. The cavity 70 may alternately decrease non-linearly in diameter. For example, the cavity may have a generally arcuate shape. According to an aspect of the invention, the maximum diameter A is between about 5% and about 20% greater than the minimum diameter B. The tapered contour of the cavity 70 forces the struts of the self-expanding stent 21 closer together, and decreases the amount of free space in the cavity 70. At the same time, the tapered contour forces the struts of the stent 21 harder against the inner surface 76 of the cover 75, resulting in increased frictional contact therebetween.

The cover 75 may comprise any suitable biocompatible material. For example, the cover 75 may comprise plastic, such as PTFE, polyethylene, nylon, or the like. The cover 75 preferably comprises a material that is sufficiently flexible so that the delivery device can negotiate and track tortuous body lumina.

According to an aspect of the invention, the inner surface 76 of the cover 75 comprises a material that has a hardness that is equal to or greater than the hardness of the stent 21. The stent 21 may be made of a metal such as 304L stainless steel, nitinol, or the like and may have a hardness that exceeds 30 Rockwell C. Accordingly, the inner surface 76 will comprise a material chosen so that the hardness of the inner surface 76 is at least as great as the hardness of the stent and may exceed 30 Rockwell C. Any suitable stent material may be used, including materials having a hardness that is less than or greater than 30 Rockwell C. Accordingly, the inner surface 76 may have a hardness that is less than or greater than 30 Rockwell C.

Figure 4C:
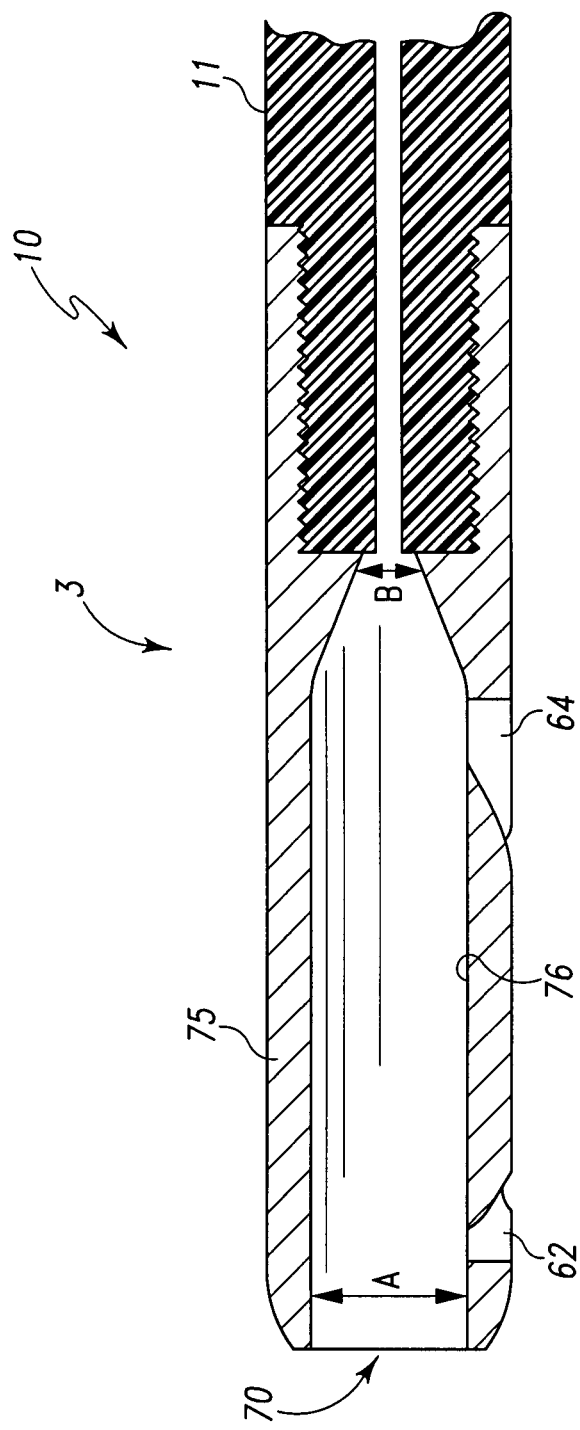
FIG. 4C is a sectional view of an alternate distal retention device according to an aspect of the invention.

FIG. 4C illustrates a retention device 10 according to an aspect of the present invention. The retention device 10 comprises a cover 75 that is adapted to retain a self-expanding stent 21 in a compressed configuration. The cover 75 comprises a cavity 70 that defines an inner radial surface 76. The cavity 70 decreases in diameter from a maximum diameter A near the distal opening to a minimum diameter B near the proximal end. The retention device 10 is threadedly connected to the flexible extension 11.

The inner surface 76 has a hardness that is equal to or greater than a hardness of the stent 21. The cover 75 may be made of commercially pure aluminum or an aluminum alloy. Commercially available grades of wrought aluminum alloys that would be suitable include, but are not limited to 1XXX, 2XXX, 3XXX, 4XXX, 5XXX, 6XXX, 7XXX, and 8XXX series aluminum alloys. Commercially available tempers that would be suitable include, but are not limited to T4, T6XXX, T7XXX, T8XXX, T9, and W. The aluminum or aluminum alloy may be treated after precipitation or age-hardening by a secondary process to provide the desirable material surface properties.

An example of a suitable secondary treatment process includes hard coat anodizing. Hard coat anodizing is a process that is well known in the art of metallurgy. A metal substrate is configured as a cathode in an electrochemical cell comprising a sulfuric acid solution. The anodizing process forms a ceramic metal oxide layer on the surface of the metal substrate. Hard coat anodizing can result in improved surface properties that include increased hardness and improved corrosion resistance. For example, anodized aluminum may have a surface hardness exceeding 60 Rockwell C. Additionally, hard coat anodizing may provide the metal substrate with a smoother, more lubricious surface.

Another example of a suitable treatment process includes hard coat anodizing with PTFE impregnation. The process is generally similar to conventional hard coat anodizing. The process differs in that the acid solution comprises a PTFE dispersion. The metal substrate forms a surface layer comprising PTFE particles impregnated in a metal oxide lattice and is smoother and more lubricious than a surface layer formed by conventional hard coat anodizing. Examples of PTFE hard-coat anodizing processes include Nituff®, developed by Nimet Industries and Hardtuf®, developed by Tiodize Co., Inc.

The cover 75 may comprise other metals, metal alloys, and/or ceramics within the scope of the present application. For example, the cover 75 may comprise any metal or metal alloy that can be anodized. Examples include, but are not limited to titanium and magnesium. Each of these materials may be anodized to form a hard metal oxide surface layer. Alternately, the cover 75 may comprise stainless steel, for example a martensitic grade such as 440A, 440B, or 440C, or a precipitation-hardenable grade such as 17-4 or 17-7. Suitable secondary treatment processes for stainless steel include carburizing, carbonitriding, nitriding, ferritic carbonitriding, and the like. Each of these processes is well known in the art of metallurgy.

Figure 4D:
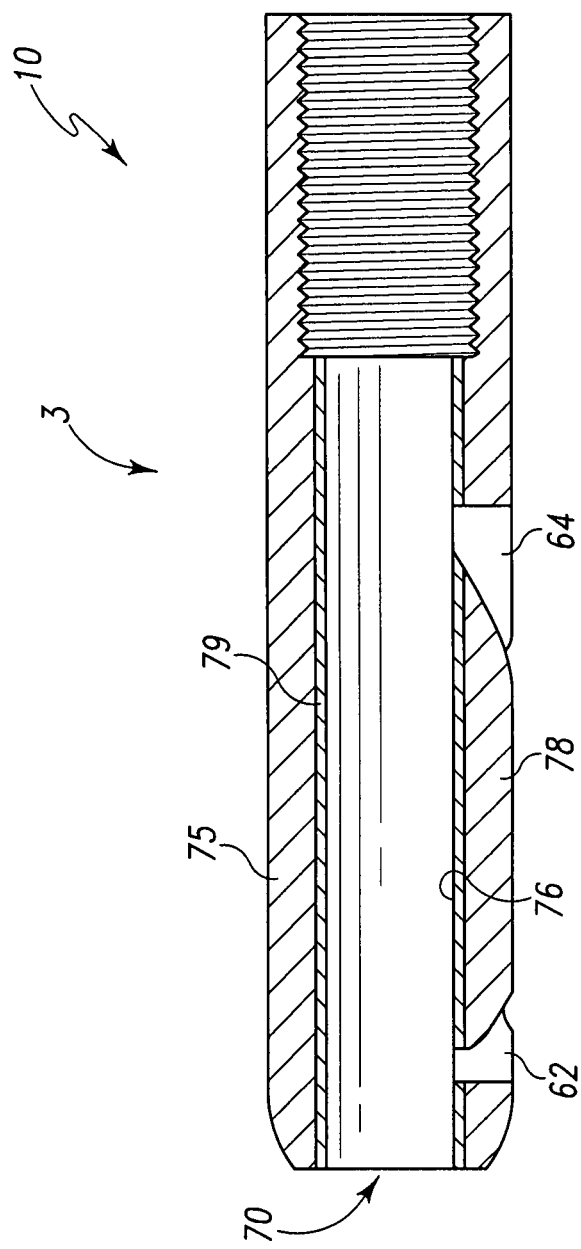
FIG. 4D is a sectional view of an alternate distal retention device according to an aspect of the invention.

FIG. 4D shows a retention device 10 according to another aspect of the invention. The cover 75 comprises a cavity 70 defining an inner radial surface 76. The cover 75 is adapted to retain a self-expanding stent 21 therein. The inner surface 76 has a hardness that is equal to or greater than the hardness of the stent 21.

As shown in FIG. 4D, the cover 75 comprises an outer portion 78 and an inner portion 79. The outer portion 78 comprises a different material than the inner portion 79. The inner portion 79 defines the inner surface 76. The outer portion 78 may comprise a low-durometer plastic, for example nylon, having a relatively low hardness. Such a material may be desirable for imparting flexibility to the delivery device. The inner portion 79, on the other hand comprises a material that is selected so that the inner surface 76 has a hardness that is equal to or greater than the hardness of the stent 21 that is used in the particular application. For example, the inner portion 79 may comprise a metal, metal alloy, or ceramic material as described above. The inner portion 79 may be treated using a secondary process to provide an inner surface 76 with desirable surface properties, as described above.

The retention device 10 is coupled to the flexible extension 11. The retention device 10 may be threadedly attached to the extension 11 (as shown in FIG. 4D). Alternately, the retention device 10 and the flexible extension 11 may be adhesively bonded or mechanically coupled to one another. For example, if the retention device 10 comprises plastic, the retention device 10 and the flexible extension may be thermally bonded to one another.

The cover 75 illustrated in FIG. 4D may be manufactured by any suitable process. For example, the outer portion 78 may comprise plastic and may be provided by a suitable process such as injection molding. The inner portion 79 may be applied to a cavity within the outer portion 78 as a metallized coating that forms inner surface 76. The metallized coating may be applied using a conventional spray or dip application process. Examples of suitable metallizing materials include, but are not limited to hard chromium, electroless nickel, brass, or copper alloys.

Another manufacturing method may include providing a plastic outer portion 78 as described above. The inner portion 79 may comprise a generally tubular bushing. The bushing may be inserted into a cavity within the outer portion 78. The bushing is fixedly attached to the outer portion 78 using convention means, including adhesive bonding or press-fitting. The tubular bushing has a lumen that defines the inner surface 76 of the cover 75. The bushing may be made of any suitable biocompatible material that has a hardness that is equal to or greater than the hardness of the stent 21. For example, the bushing may comprise an anodized metal or a hardened alloy steel such as 52100 steel. The bushing may alternately comprise a carbon or low alloy steel that has been treated by nitriding, ferritic carbonitriding, carbonitriding, or a like process.

FIG. 5 shows the haemostatic sealing means 35 of the external manipulation section 1 in greater detail. The haemostatic sealing means 35 comprises a haemostatic seal 27 and a clamping collar 23 that clamps the sheath 30 to the haemostatic seal 27. The haemostatic seal 27 may include a silicone seal ring 28. The silicone seal ring 28 forms a haemostatic seal around the thick walled tube 41. The haemostatic sealing means 35 may include a side tube 29. The side tube 29 facilitates the introduction of medical reagents between the thick walled tube 41 and the sheath 30.

Figure 6:
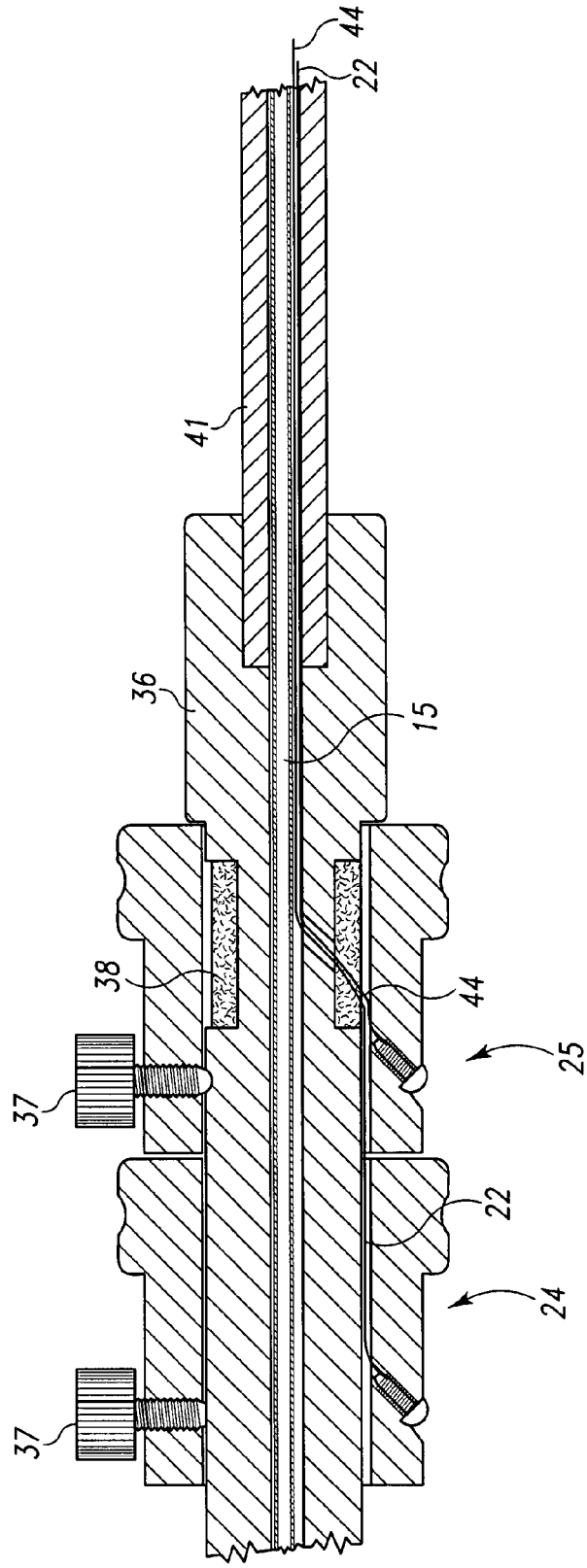
FIG. 6 is a sectional view of a portion of the delivery device of FIG. 1 around the trigger wire release mechanism.

As shown in FIG. 6, the distal trigger wire 22 extends through the annular space between the thick walled tube 41 and the thin walled tube 15 to the manipulation region 1. The distal trigger wire 22 exits the annular space at a distal wire release mechanism 24. The self-expanding stent 21 is released by retracting the sheath 30, removing the trigger wire 22, and then sliding the distal attachment region 3, including the retention device 10, distally away from the stent 21. Once the retention device 10 has cleared the self-expanding stent 21, the stent 21 will expand. The suture loops 66, the trigger wire 22, and the distal wire release mechanism 24 form a control member to selectively release the retention device 10 from the prosthesis 20 by holding the self-expanding stent 21 in the retention device 10 until the prosthesis 20 is positioned at a desired site in the lumen.

The proximal trigger wire 44 extends through the annular space between the thick walled tube 41 and the thin walled tube 15 to the manipulation region. The proximal trigger wire 44 exits the annular space at a proximal wire release mechanism 25. The proximal trigger wire 44 and the proximal wire release mechanism 25 form a control member to selectively release the proximal retention section 40 from the prosthesis when the prosthesis is positioned at a desired site in the lumen.

The release wire actuation section has a body 36 that is mounted onto the thick walled plastic tube 41, as shown in FIG. 6. The thin walled tube 15 passes through the body 36. The proximal wire release mechanism 25 is mounted for slidable movement on the body 36. A clamping screw 37 prevents inadvertent early release of the proximal end 42 of the prosthesis 20. Similarly, the distal wire release mechanism 24 is mounted for slidable movement on the body 36. A clamping screw 37 prevents inadvertent early release of the self-expanding zigzag stent 21 of the prosthesis 20.

The positioning of the distal and proximal wire release mechanisms 24 and 25 is such that the distal wire release mechanism 24 must be moved before the proximal wire release mechanism 25 can be moved. Therefore, the proximal end of the prosthesis 20 cannot be released until the self-expanding zigzag stent 21 has been released and anchored to the lumen. A haemostatic seal 38 is provided so the release wire 44 can extend out through the body 36 to the release mechanism 25 without unnecessary blood loss during the medical procedure.

FIG. 7 shows a proximal portion of the external manipulation section 1. A pin vise 39 is mounted onto the proximal end of the body 36. The pin vise has a screw cap 46. When screwed in, the vise jaws 47 clamp against (engage) the thin walled metal tube 15. When the vise jaws 47 are engaged, the thin walled tube 15 can only move with the body 36, and hence the thin walled tube 15 can only move with the thick walled tube 41 (not shown). With the screw cap 46 tightened, the entire assembly, except for the external sleeve 30, can be moved as one.

The various stages of delivery and deployment of the prosthesis 20 will now be explained with reference to FIGS. 8 through 11. A guide wire 13 is introduced, for example, into the femoral artery and is advanced until the tip of the guide wire 13 is beyond the region into which the prosthesis 20 is to be deployed. The delivery device is then inserted through the femoral artery over the guide wire 13, and positioned by radiographic techniques, generally known in the art. At this stage, the ends of the prosthesis 20 are retained by the distal and proximal retaining assemblies respectively and the sheath 30 is disposed over and covers the length of the prosthesis 20. The self-expanding stent 21 is compressed within the cover 75.

Figure 8:
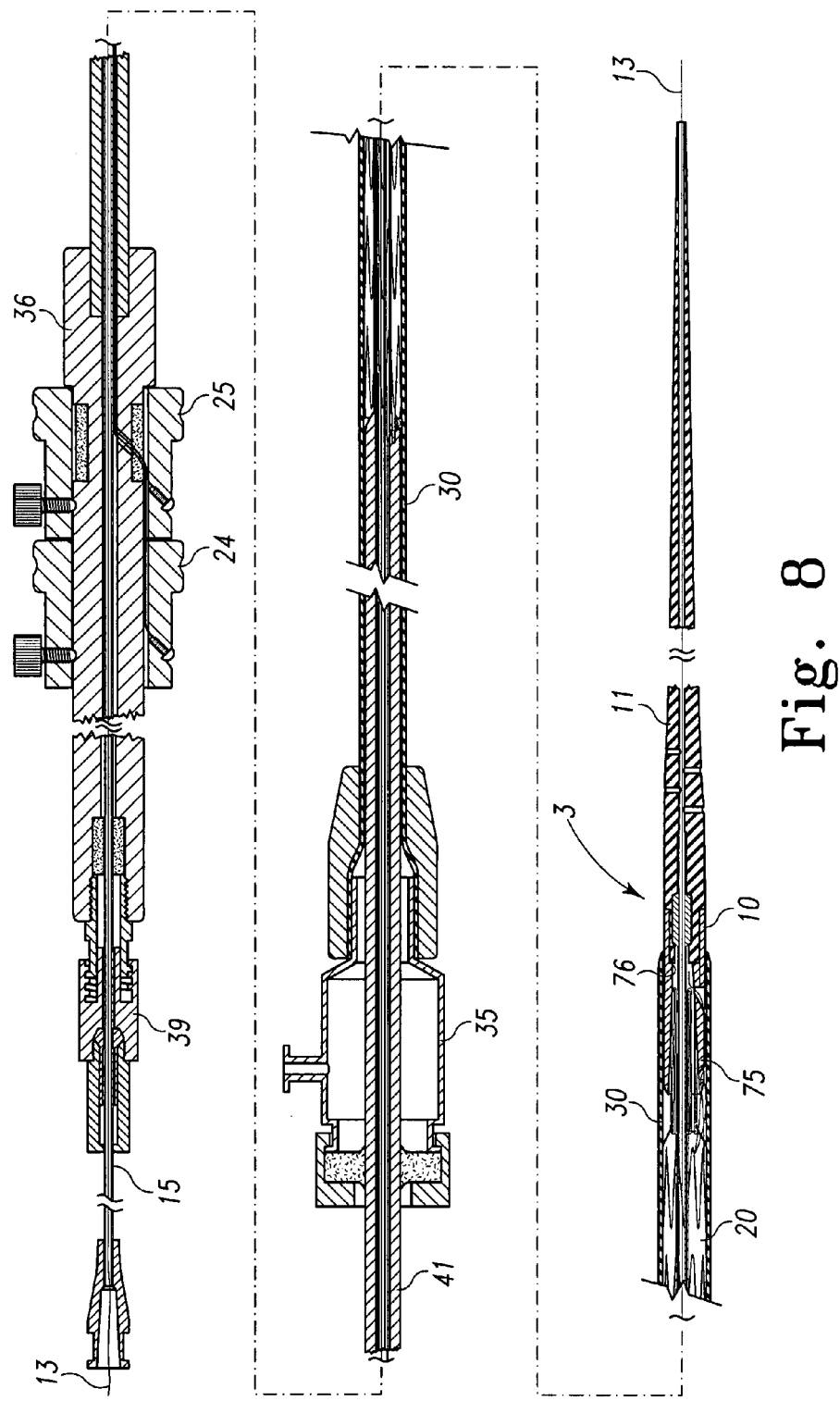
FIG. 8 is a segmented sectional view of the delivery device of FIG. 1, fully loaded and ready for introduction into a patient.
Figure 9:
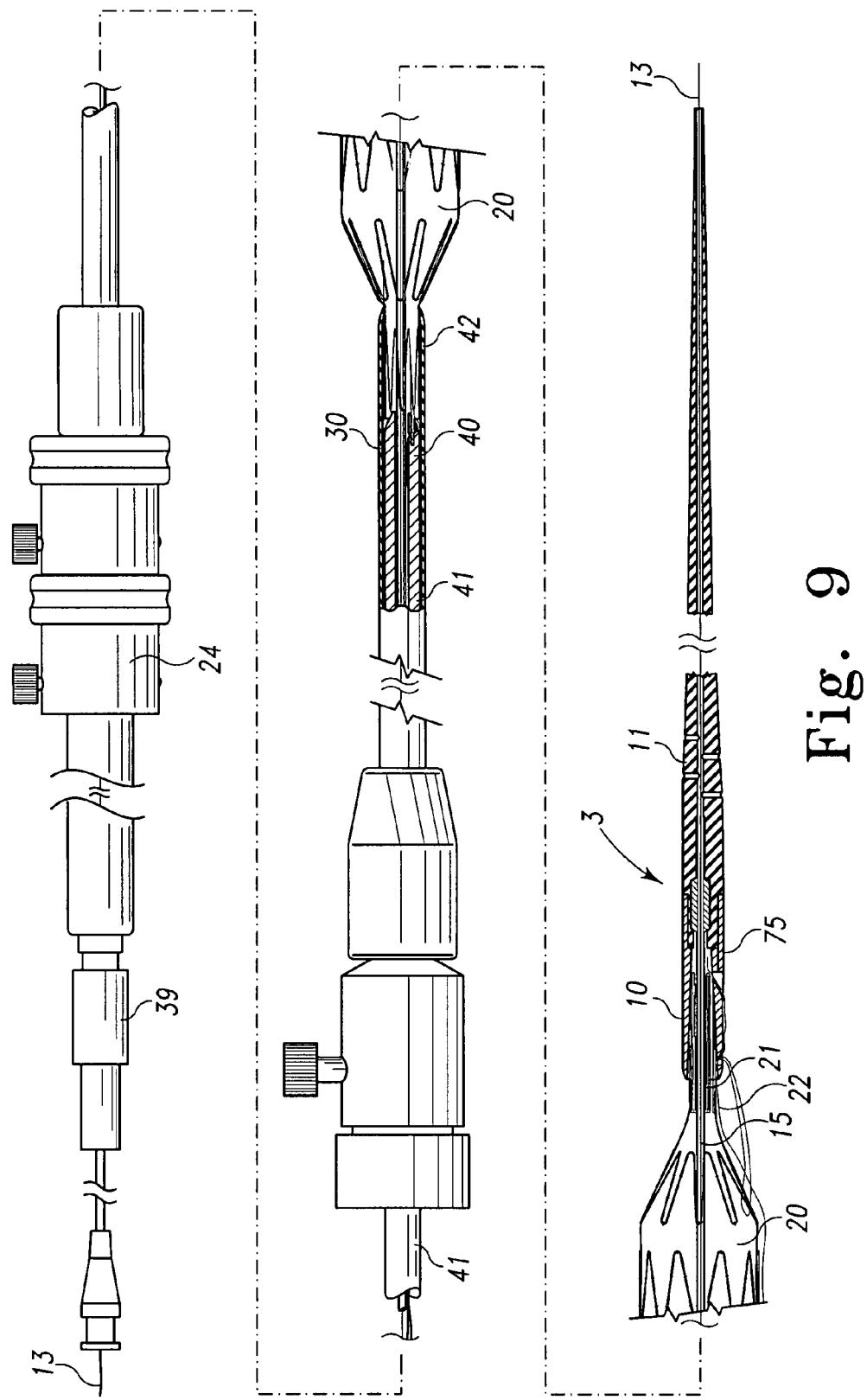
FIG. 9 is a segmented sectional view of the delivery device of FIG. 1, demonstrating the prosthesis in an initial stage of deployment.

In FIG. 8, the delivery device is shown fully assembled ready for introduction into a patient. The ends of the prosthesis 20 are retained by the distal and proximal retaining assemblies respectively, while the sheath 30 compresses the middle portion of the prosthesis intermediate the ends. Once the delivery device is in a desired position for deployment of the prosthesis 20, the sheath 30 can be withdrawn to just distal of the proximal attachment section 40, as shown in FIG. 9. This action exposes the middle portion of the prosthesis 20 so that the middle portion can expand radially outwardly. The self-expanding stent 21, however, is still retained within the cover 75 of the retention device 10. Also, the proximal end of the prosthesis 20 is still retained within the sheath 30.

Next, the pin vise 39 is released to allow small movements of the thin walled tubing 15 with respect to the thick walled tubing. In this way, the prosthesis 20 may be lengthened or shortened or rotated or compressed for accurate placement in the desired location within the lumen. X-ray opaque markers (not shown) may be placed along the prosthesis 20 to assist with placement of the prosthesis.

Figure 10:
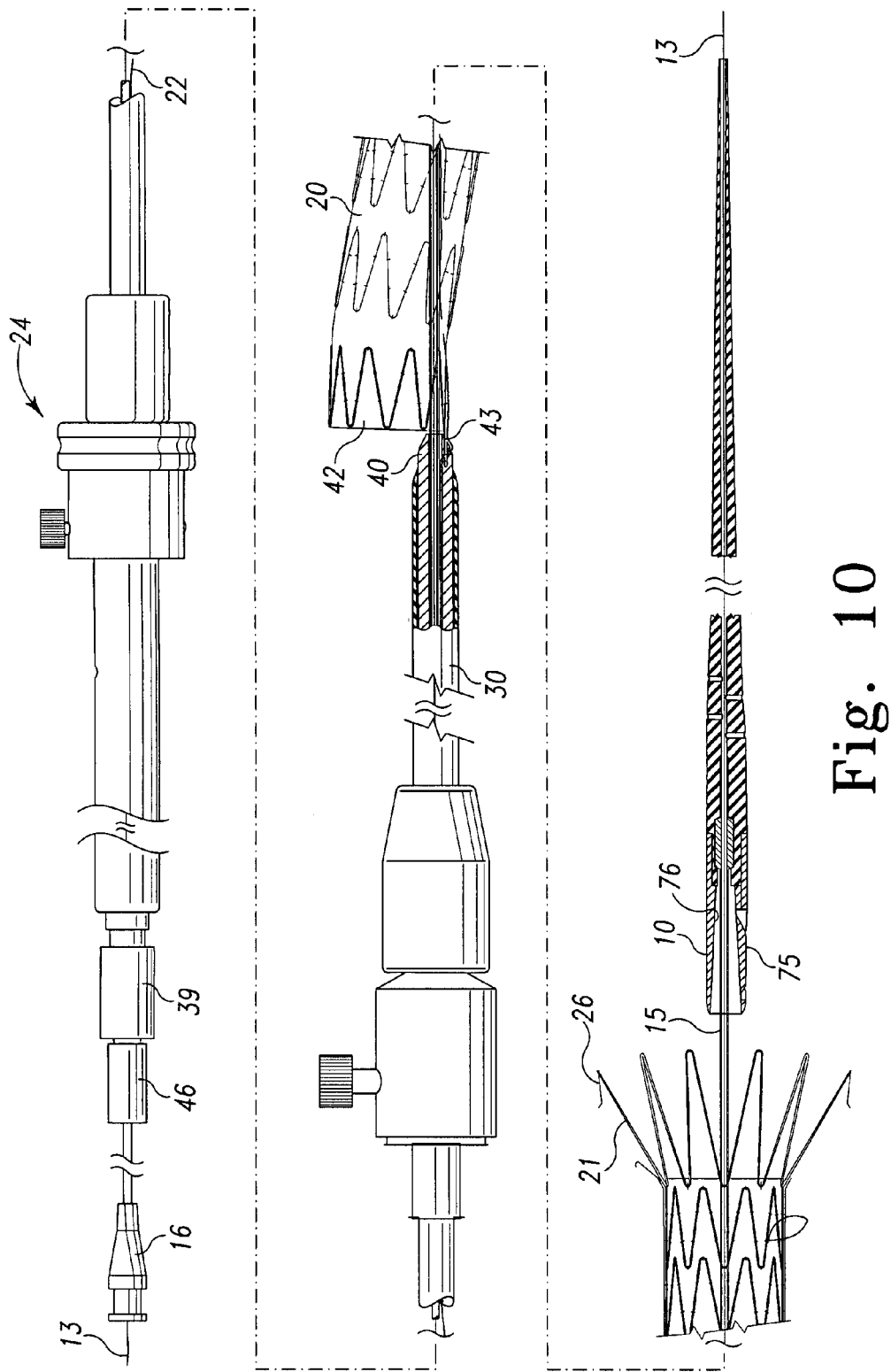
FIG. 10 is a segmented sectional view of the delivery device of FIG. 1, demonstrating the release of the prosthesis distal end during deployment.

In FIG. 10, the distal trigger wire 22 has been removed, allowing the cover 75 to be separated from the self-expanding zigzag stent 21, as explained above. At this stage, the distal trigger wire release mechanism 24 and the distal trigger wire 22 can be removed completely. The screw cap 46 of the pin vise 39 has been loosened so that the thin walled tubing 15 can be pushed in a distal direction to move the cover 75 in a distal direction with respect to the stent 21. When the cover 75 no longer surrounds the self-expanding stent 21 at the distal end of the prosthesis 20, the self-expanding stent 21 expands. When the self-expanding stent 21 expands, the barbs 26 grip into the walls of the lumen to hold the proximal end of the prosthesis 20 in place.

At this point, the proximal end of the prosthesis 20 is still retained by the proximal retention section 40 with the loop 43 retained therein. The sheath 30 is then withdrawn to proximal of the proximal retention section 40 to allow the proximal end of the prosthesis 20 to expand. At this point, the proximal end of the prosthesis may still be moved. Consequently, the prosthesis 20 can still be rotated or lengthened or shortened or otherwise moved for accurate positioning. Where the prosthesis 20 to be deployed is a bifurcated graft, the movement at this stage may ensure that the shorter leg is directed in the direction of the contra-iliac artery.

Figure 11:
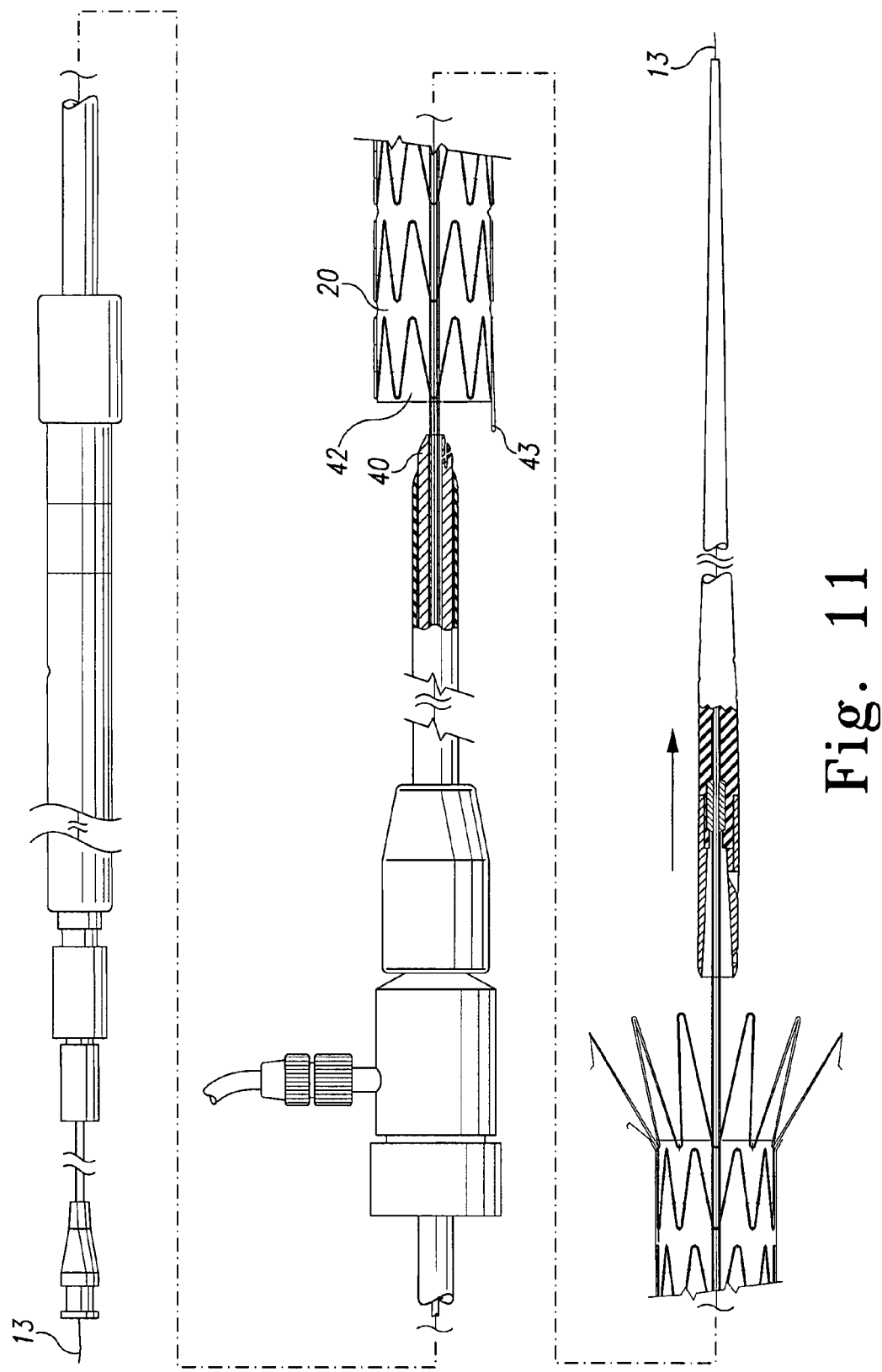
FIG. 11 is a segmented sectional view of the delivery device of FIG. 1, demonstrating the release of the prosthesis proximal end during deployment.

In FIG. 11, the proximal end 42 of the prosthesis 20 has been released by the removal of the proximal trigger wire 44. At this stage, the proximal trigger wire release mechanism 25 and the proximal trigger wire 44 can be removed completely. This removal may be accomplished by passing the proximal wire release mechanism 25 over the pin vise 39 and the connection means 16. The loop 43 of the terminal proximal self-expanding zigzag stent 19 is hence released, and the prosthesis is now free to expand to the walls of the vessel. At this point, the delivery device is ready to be removed. The sheath 30 may be removed with the distal attachment device 10, the tapered flexible extension 11 and the proximal attachment device 10. Alternatively, these items could be removed separately, followed by removal of the external sleeve 30.

Throughout this specification, unless the context requires otherwise, the words "comprise", "include", and "have" and variations such as "comprising", "including", and "having" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the appended claims and their equivalents.

What is claimed is:

1. A system for endoluminally delivering and deploying a prosthesis, the system comprising:
   a prosthesis having an end portion and a body portion, the end portion including a self-expanding stent having a hardness; and
   a cover for maintaining at least a portion of the stent in a compressed state until deployment, the cover having a generally tubular cavity with an inner surface, wherein the stent is biased into contact with the inner surface of the cover, the inner surface having a hardness that is equal to or greater than the hardness of the stent, wherein the inner surface comprises a ceramic material.

2. The system according to claim 1, wherein the inner surface further comprises PTFE.

3. The system according to claim 1, wherein the stent is made from a metal selected from stainless steel and nitinol.

4. The system according to claim 1, wherein the stent further comprises a plurality of radially-disposed barbs.

5. The system according to claim 1, further comprising a sheath having a sheath lumen, wherein at least a portion of the prosthesis is radially disposed within the sheath lumen in a compressed configuration.

6. The delivery device according to claim 1 wherein:
   the inner surface further comprises PTFE;
   the stent comprises a plurality of radially-disposed barbs and is made from a metal selected from stainless steel and nitinol; and
   the system further comprises a sheath having a sheath lumen, wherein at least a portion of the prosthesis is radially disposed within the sheath lumen in a compressed configuration.

7. A system for endoluminally delivering and deploying a prosthesis, the system comprising:
   a prosthesis having an end portion and a body portion, the end portion including a self-expanding stent having a hardness; and
   a cover for maintaining at least a portion of the stent in a compressed state until deployment, the cover having a generally tubular cavity with an inner surface, wherein the stent is biased into contact with the inner surface of the cover, the inner surface having a hardness that is equal to or greater than the hardness of the stent, wherein the cover comprises a plastic body with a ceramic inner surface.

8. A method of manufacturing an endoluminal prosthesis delivery and deployment system, the method comprising the steps of:
   providing a prosthesis having a proximal end and a distal end, at least one of the proximal and distal ends including a self-expanding stent having a hardness;
   providing a cover having a cavity defining an inner surface, the inner surface having a hardness that is equal to or greater than the hardness of the stent; and retaining at least a portion of the stent within the cavity so that the stent is biased into contact with the inner surface, wherein the cover providing step comprises providing a ceramic inner surface.

9. The method according to claim 8, wherein the cover providing step further comprises providing an inner surface that includes PTFE.

10. The method according to claim 8, wherein the cover providing step comprises inserting a metal bushing into the cavity, the bushing having an inner lumen that defines the inner surface of the cover.

* * * * *